United States Patent [19]

Howe

[11] Patent Number: 5,170,064
[45] Date of Patent: Dec. 8, 1992

[54] INFRARED-BASED GAS DETECTOR USING A CAVITY HAVING ELLIPTICAL REFLECTING SURFACE

[75] Inventor: Philip T. Howe, Pinawa, Canada

[73] Assignee: Atomic Energy of Canada Limited, Canada

[21] Appl. No.: 720,428

[22] PCT Filed: Sep. 10, 1990

[86] PCT No.: PCT/CA90/00288
 § 371 Date: Jun. 26, 1991
 § 102(e) Date: Jun. 26, 1991

[87] PCT Pub. No.: WO91/05240
 PCT Pub. Date: Apr. 18, 1991

[30] Foreign Application Priority Data

Sep. 29, 1989 [CA] Canada ................................... 615091
Sep. 29, 1989 [CA] Canada ................................... 615459

[51] Int. Cl.⁵ ............................................. G01N 15/06
[52] U.S. Cl. ................................. 250/573; 250/228; 250/343
[58] Field of Search ............... 250/228, 343, 345, 573, 250/574, 575, 576; 356/236, 437–440

[56] References Cited

U.S. PATENT DOCUMENTS

| | | |
|---|---|---|
| 3,238,470 | 3/1966 | Mooney . |
| 3,266,313 | 8/1966 | Litterst . |
| 3,359,509 | 12/1967 | Hall . |
| 3,588,739 | 6/1971 | Yoshikawa et al. . |
| 3,694,086 | 9/1972 | May ........................ 356/51 |
| 3,745,325 | 7/1973 | Harvey ................... 240/1.3 |
| 3,784,836 | 1/1974 | Tolliver ................. 250/495 |
| 3,822,097 | 7/1974 | Allington ............... 250/226 |
| 3,959,660 | 5/1976 | Tolliver ................. 250/343 |
| 4,158,772 | 6/1979 | Reedy .................... 356/244 |
| 4,355,233 | 10/1982 | Warnke et al. ....... 250/343 |
| 4,360,275 | 11/1982 | Louderback .......... 356/446 |
| 4,468,561 | 8/1984 | Speeter ................. 250/345 |
| 4,557,603 | 12/1985 | Oehler et al. ......... 250/343 |
| 4,657,397 | 4/1987 | Oehler et al. ......... 356/436 |
| 4,740,086 | 4/1988 | Oehler et al. ......... 250/343 |
| 4,808,825 | 2/1989 | Miyatake et al. .... 250/343 |
| 4,810,658 | 3/1989 | Shanks et al. ........ 356/440 |
| 4,818,882 | 4/1989 | Nexo et al. ............ 250/343 |
| 4,868,383 | 9/1989 | Kurtz et al. ........... 250/228 |
| 4,873,430 | 10/1989 | Juliana et al. ......... 250/228 |

FOREIGN PATENT DOCUMENTS

| | | |
|---|---|---|
| 647204 | 8/1962 | Canada . |
| 851284 | 9/1970 | Canada . |
| 866311 | 3/1971 | Canada . |
| 1083380 | 8/1980 | Canada . |
| 1092848 | 1/1981 | Canada . |
| 1126977 | 7/1982 | Canada . |
| 1127867 | 7/1982 | Canada . |
| 1135971 | 11/1982 | Canada . |
| 1136883 | 12/1982 | Canada . |
| 1177665 | 11/1984 | Canada . |
| 1183897 | 3/1985 | Canada . |
| 1187717 | 5/1985 | Canada . |
| 1228748 | 11/1987 | Canada . |

Primary Examiner—David C. Nelms
Assistant Examiner—S. Allen
Attorney, Agent, or Firm—Davis, Bujold & Streck

[57] ABSTRACT

A nondispersive gas analyzer for use in monitoring the concentration of one or more gases, comprises a body having a cavity having an elliptical reflecting surface, defining a first focus and a second focus, for transmitting radiation between the focuses, a chamber (2) for holding a sample gas to be analyzed, one of the focuses being located within the sample chamber, a chamber (4) for holding an inert gas and a chamber (3) for holding an analyte gas, a radiation source (24) disposed at one of the focuses, and a radiation detector (26, 27) associated with each of the inert and analyte gas chambers for detecting the radiation passing through the sample gas and the inert gas and the radiation passing through the sample gas and the analyte gas located at the other of the focuses.

27 Claims, 6 Drawing Sheets

INFRARED-BASED GAS DETECTOR USING A CAVITY HAVING ELLIPTICAL REFLECTING SURFACE

FIELD OF THE INVENTION

This invention relates to a nondispersive analyzer, which can be used to monitor the concentration of one or more gases.

BACKGROUND OF THE INVENTION

Nondispersive analyzers are analyzers which provide discrete radiation paths from a source to one or more means for detecting the intensity of radiation. One of these paths is through the sample to be analyzed as well as through an isolated fixed quantity of the analyte gas, and another of these paths is through the sample to be analyzed only. Therefore, that part of the radiation which is at the wavelengths absorbed by the analyte gas is removed from one path, but not the other, resulting in a difference in the outputs from the energy detecting means associated with these paths. Thus, it is only when the sample contains the analyte gas that the difference between the intensities of the radiation along the two paths will be reduced. Other absorbing compounds affect both detectors equally.

In order to ensure that error is not introduced by reason of some variation between radiation sources, a single source is usually used to generate the beams of radiation over both paths. Thus, a beam splitter or chopper is required. Analyzers of this sort may be relatively large. Further, appreciable energy is consumed, often of the order of tens of watts. This is required to power the source, to operate the chopper motor for the beam splitter, and to power the measuring circuits.

This invention provides a nondispersive analyzer which is relatively small and light in weight, and which does not require either a beam splitter or a mechanical chopper. It requires very little power, approximately one watt, and that only intermittently. It can therefore be operated for several weeks on the energy stored in a lightweight battery. It uses an elliptical reflector to focus light from its energy source.

Elliptical cylinder and ellipsoidal reflectors are commonly used in optics to focus light. Such reflectors are frequently used in measuring devices. Thus U.S. Pat.No. 3,266,313 (Litterest) shows a temperature measuring device where the object whose temperature is to be measured (a wire) is at one focus of an ellipse and the detector is at another focus. U.S. Pat. No. 4,810,658 (Shanks) shows in FIG. 4a a system where a liquid sample in contact with a solid wave guide is placed at one focus of an ellipse and a light source at the other focus.

Partially elliptical or ellipsoidal mirrors are shown in Canadian Patents 1,126,977 (Hogg) and 1,127,867 (Brunsting) for particle counters. The sample and light source are located at one focus of the ellipse. A detector is located either on the axis of the two foci (in Brunsteig) or is reflected off this axis by a mirror (in Hogg).

C.P. 1,228,748 (Oetliker) shows a variety of light guiding designs for various purposes using ellipsoids. In some of the designs the light source and the sample are at one focus of an ellipsoid and a detector is at the other focus. In other designs, a light source is at one focus and a specimen to be treated by light (as for example in a chemical process) is at the second focus.

Elliptical or ellipsoidal reflectors are not common in spectrometry. Three patents of Oehler, U.S. Pat. Nos. 4,557,603; 4,657,397 and 4,740,086 and one of Miyatake (U. S. Pat. No. 4,808,825) disclose infrared spectrophotometers. However, such spectrophotometers are not of the non-dispersive type, and have only one gas cell which is traversed by the light. They do not assist in the design of a non-dispersive gas analyzer, where light rays must pass through several gas cells to give a comparative measurement.

SUMMARY OF THE INVENTION

According to the present invention, there is provided an analyzer which comprises a body having a cavity having an elliptical reflecting surface means, which defines a first focus and a second focus, for transmitting radiation between the focuses, a chamber for holding a sample gas to be analyzed, one of the focuses being located within the sample chamber, a chamber for holding an inert gas and a chamber for holding an analyte gas, the inert gas and analyte gas chambers being positioned along a path extending between the second focus and at least a portion of the reflecting surface means; a radiation source disposed at one of the focuses; and detector means associated with each inert gas chamber and analyte chamber for detecting radiation passing through the sample gas and and its associated gas chamber.

The chambers are so positioned so that radiation focused by the elliptical reflecting surface will always pass through the sample chamber and either the analyte chamber or the inert gas chamber as it travels to a detecting means. In certain embodiments of the invention, there is a plurality of analyte chambers and detectors, so that the sample gas can be analyzed for several different components (analytes). This invention can be applied, for example, to monitoring air quality, detecting leakage, or as the sensing element in a flow control system.

DETAILED DESCRIPTION OF PREFERRED EMBODIMENTS

Figure 1:
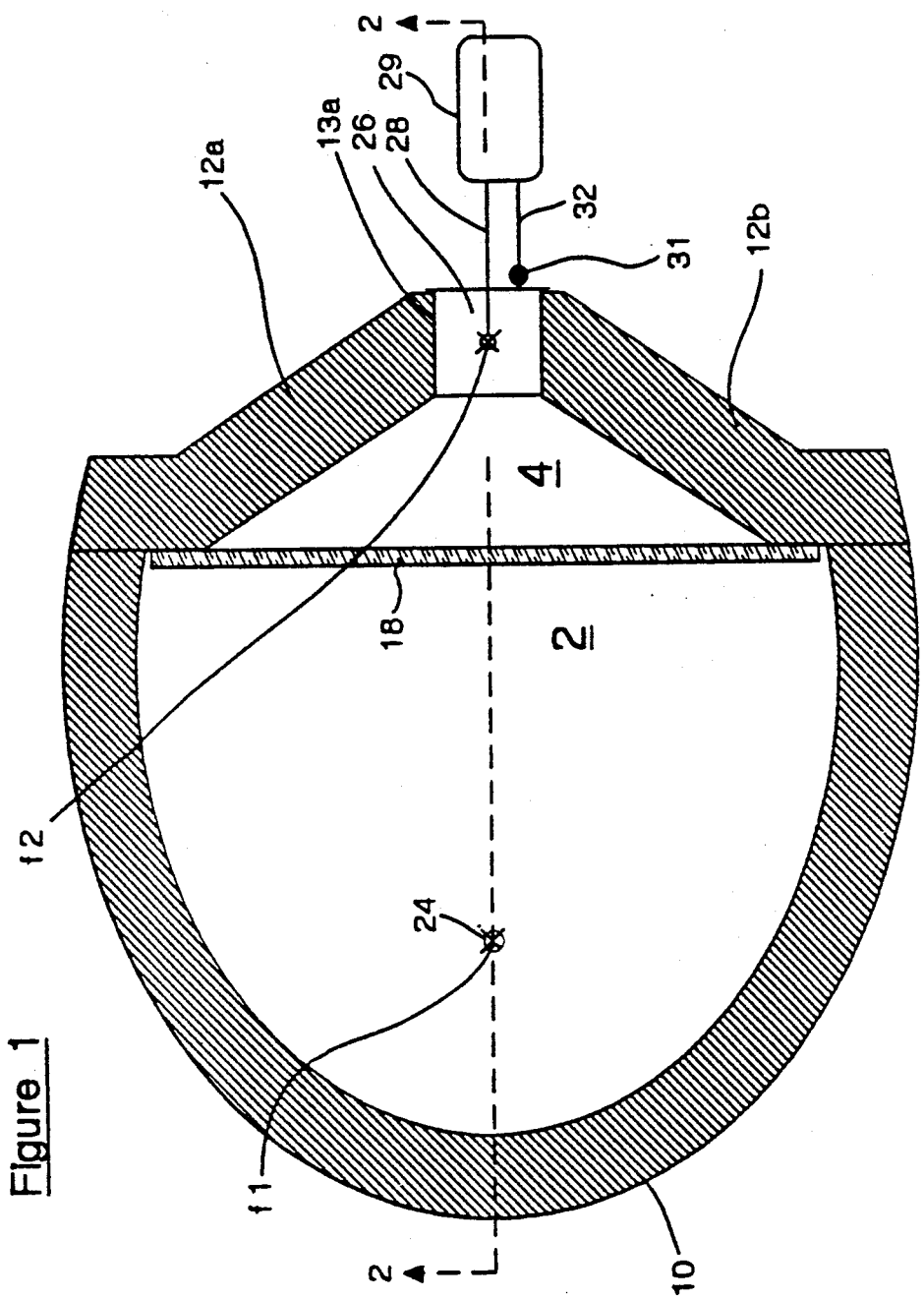
FIG. 1 is a cross-sectional plan view of one embodiment of the novel analyzer, taken on the line 1—1 of FIG. 2.
Figure 2:
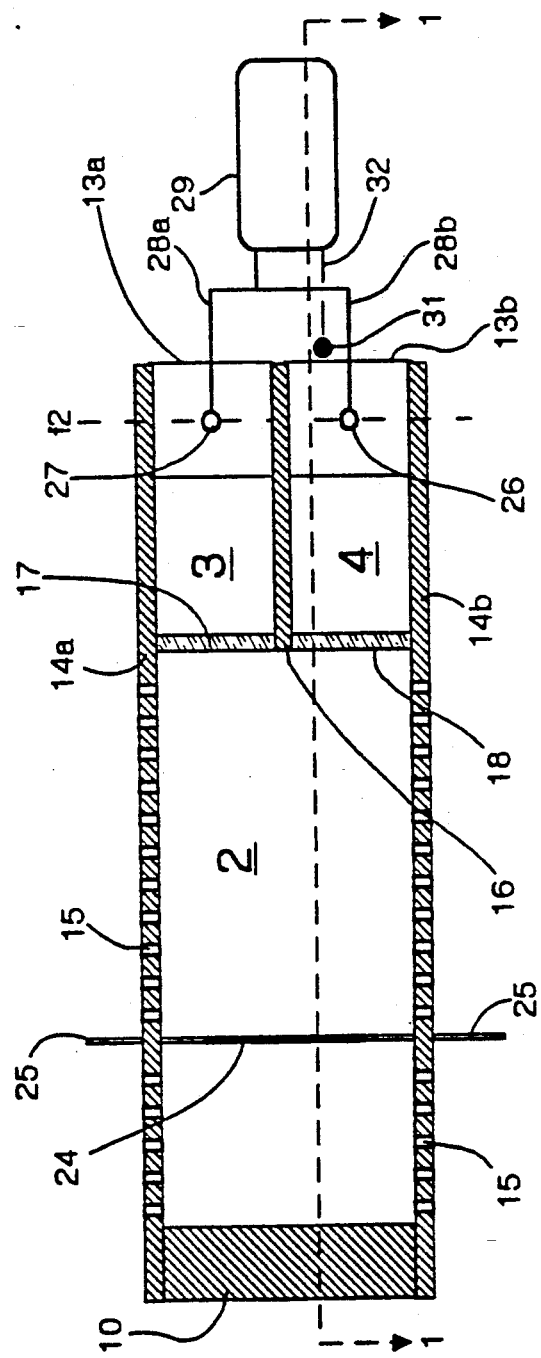
FIG. 2 is a cross-sectional side view of the same embodiment, taken on the line 2—2 of FIG. 1.

FIGS. 1 and 2 show an analyzer for analyzing the content of one particular gas in an unknown sample. For example, the sample may be ambient air, and carbon dioxide may be the gas whose concentration is to be measured.

An analyzer housing (not shown) is provided. Within the housing is a chamber 2 (hereinafter called the sample chamber) to contain the sample to be analyzed, a chamber 3 (hereinafter called the analyte chamber) containing the analyte gas, and a chamber 4 (hereinafter called the inert gas chamber) to contain an inert gas, which may suitably be the sample gas which does not contain the analyte gas. The chamber 2 comprises a side wall 10, two end portions 12a and 12b top wall 14a and bottom wall 14b. The side wall 10 is a portion of an ellipse, with its foci at f1 and f2. The end portions terminate in two openings 13a and 13b. The shape of the two end portions 12a and 12b is not critical, and they can be elliptical if desired. Their purpose is to close the open side of the elliptical reflector and to form two openings 13a and 13b which support the detectors. Suitably, the side wall is a material which efficiently reflects radiation, for example polished aluminum, or a composite material coated with a reflective material.

The top portion of the side wall 10 mates with top wall 14a. The bottom portion mates with bottom wall 14b. The top and bottom walls are made of a suitably reflective material, such as polished aluminum.

Each of walls 14a and 14b is provided with a plurality of holes 15, to permit the sample gas to enter and leave the device. If the device is used as an air tester, the sample gas will normally be the ambient air being tested.

In the region bounded by the end portions 12a and 12b there is a divider wall 16, parallel to the top and bottom walls. Preferably, the divider is located midway between the top and bottom walls.

Two windows 17 and 18 extend in gas tight relation between the top wall 14a and the bottom wall 14b and the divider wall 16. These windows can be made from any gas impermeable material that is substantially transparent at the wavelengths at which the analyte absorbs, as is known in the art. For example, sapphire or potassium bromide are suitable materials when measuring the carbon dioxide content of air by infrared absorption.

At the focus f1 of the ellipse, within chamber 2, is situated radiation source 24. The source is preferably linear and small in cross section. If the analyzer is to use infrared radiation, it can be a conventional gas chromatograph thermal conductivity detector element. One suitable such element is a Gow-Mac #13-470P element. Suitable wiring 25 leads from the source 24 through the bottom and/or top walls to a suitable power source and control circuit.

At the focus f2 of the ellipse, in gas-tight seal in the openings 13a and 13b, are placed two detectors.

The top wall 14a, elliptical side wall 10 and bottom wall 14b, together with windows 17 and 18, define the sample chamber 2. The detector 27, window 17, top wall 14a and divider wall 16, together with side walls 12, define the analyte chamber 3. The detector 26, the window 18, bottom wall 14b and divider wall 16, together with side walls 12, define the inert gas chamber 4. These detectors can be any detector compatible with the wavelength of the radiation and the wavelengths absorbed by the analyte. For example, when the analyzer is to be used to analyze carbon dioxide in air, the detectors can be thermopile detectors, thermistors, or pyroelectric detectors. One suitable detector for such analysis is, for example, a model 2M thermopile detector obtained from Dexter Research Centre.

The radiation source 24, and the detectors 26 and 27, are placed respectively as precisely as possible on foci f1 and f2 of the elliptical reflector 10.

The detectors are connected by suitable wiring 28a and 28b to a suitable instrument control and data collection apparatus 29. For example, the apparatus 29 can include a microprocessor connected and programmed to control the timing and switching functions necessary for operating the instrument, to store and analyze the data, and to display the processed data as required.

A suitable power supply (not shown) is provided for the radiation source 24 and the instrument control and data collection apparatus 29. Such a suitable power supply can be, for example, several AA size alkaline cells connected in series and/or parallel.

If it is desired to correct for changes in ambient temperature, a thermistor 31 can be placed in close proximity to the detectors, and its response used in the known way to compensate the data collection apparatus 29 by wiring 32.

A suitable means for confirming proper operation of the instrument can be provided if desired. This can be done, for example, by providing a screen with known radiation removal characteristics, which can be moved into the beam passing from the radiation source to one detector. The detector reading should then vary in the known manner from the screen characteristics.

Prior to operation, the analyte chamber 3 is filled with the analyte gas and the inert gas chamber 4 is filled with inert gas. For example, if it is intended to measure the concentration of carbon dioxide in ambient air, air with the carbon dioxide removed can be used in chamber 4 and chamber 3 is filled with carbon dioxide.

The gas mixture to be analyzed is allowed to diffuse, or is otherwise introduced, into chamber 2 through holes 15. The radiation source is energized. Since sidewall 10 is elliptical in shape, with the source 24 located at one focus f1, the radiation emitted from source 24 is focused at f2. A portion of such radiation passes through sample chamber 2 and analyte chamber 3 to impinge on detector 27 at f2. A further portion passes through sample chamber 2 and inert gas chamber 4 to impinge on detector 26.

This focusing by the elliptical reflector permits detector readings to be obtained with little expenditure of energy, allowing a relatively low-powered radiation source to be used. It has been found, for example, that the source, the detectors and the data collection and analysis device can be operated in one embodiment on a total power of approximately 400 mw.

The data received from the two detectors 26 and 27 are analyzed in known fashion. If the unknown sample in sample chamber 2 does not contain the analyte gas, the difference between the output of detectors 26 and 27 will remain at a fixed known value (when corrected for temperature variation by means of thermistor 31). If, however, there is some of the analyte gas in the sample in sample chamber 2, the difference between the readings of detectors 26 and 27 will exhibit a reduced value characteristic of the concentration of the analyte in sample chamber 2.

Figure 3:
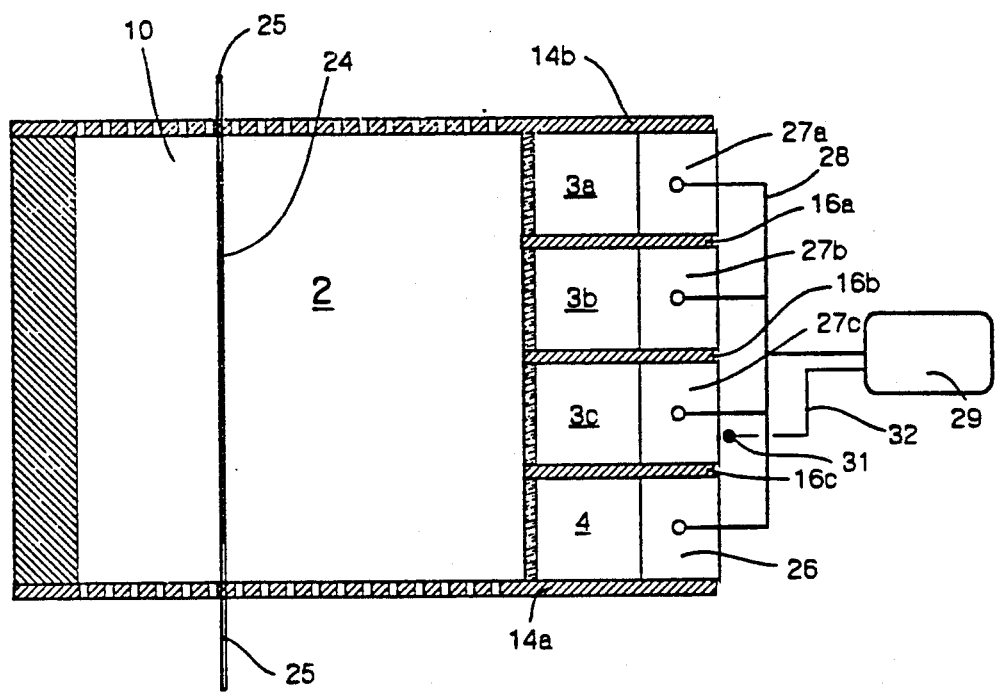
FIG. 3 is a cross-sectional side view similar to FIG. 2, of a different embodiment, which can be used to analyze a sample simultaneously for three different gases.

FIG. 3 shows an embodiment in which analysis is carried out simultaneously for three analyte gases. In that Figure, the same numbering is used as in FIGS. 1 and 2 where parts are the same. However, instead of the single analyte chamber 3, three analyte chambers 3a, 3b, and 3c, for three different analytes are provided, and these are separated by walls 16a, 16b, and 16c. As before, chamber 4 contains a gas which is inert with respect to the measurement to be made. If the device is to analyze air, the inert gas can be air from which the analyte gases have been removed. Four detectors 27a, 27b, 27c, and 26 are provided on the focus f2 to measure the radiation passing through the chambers 3a, 3b, 3c, and 4.

As will be noted from the description, only a portion of wall 10 need be elliptical. Even a small segment of an elliptical wall is helpful, as it will direct some of the energy from the radiation source as a beam directed to the detectors. Generally, it is preferred that the wall 10 form at least one-quarter of an ellipse, and that this be at the end of the device proximate to the focus f1 and remote from the focus f2. However, the device can be arranged with wall 10 as a full ellipse. Alternately, walls 10, 14a and 14b can together form an ellipsoid, or a portion of an ellipsoid, to further focus the radiations.

The analyzer has been described with respect to a source of infrared radiation, and a detector for such radiation. However, depending on the intended analyte, it may be preferable to have the radiation source 24 as a visible or ultraviolet light bulb or light pipe from an external bulb, and to have a suitable detector for ultraviolet or visible light.

Figure 4:
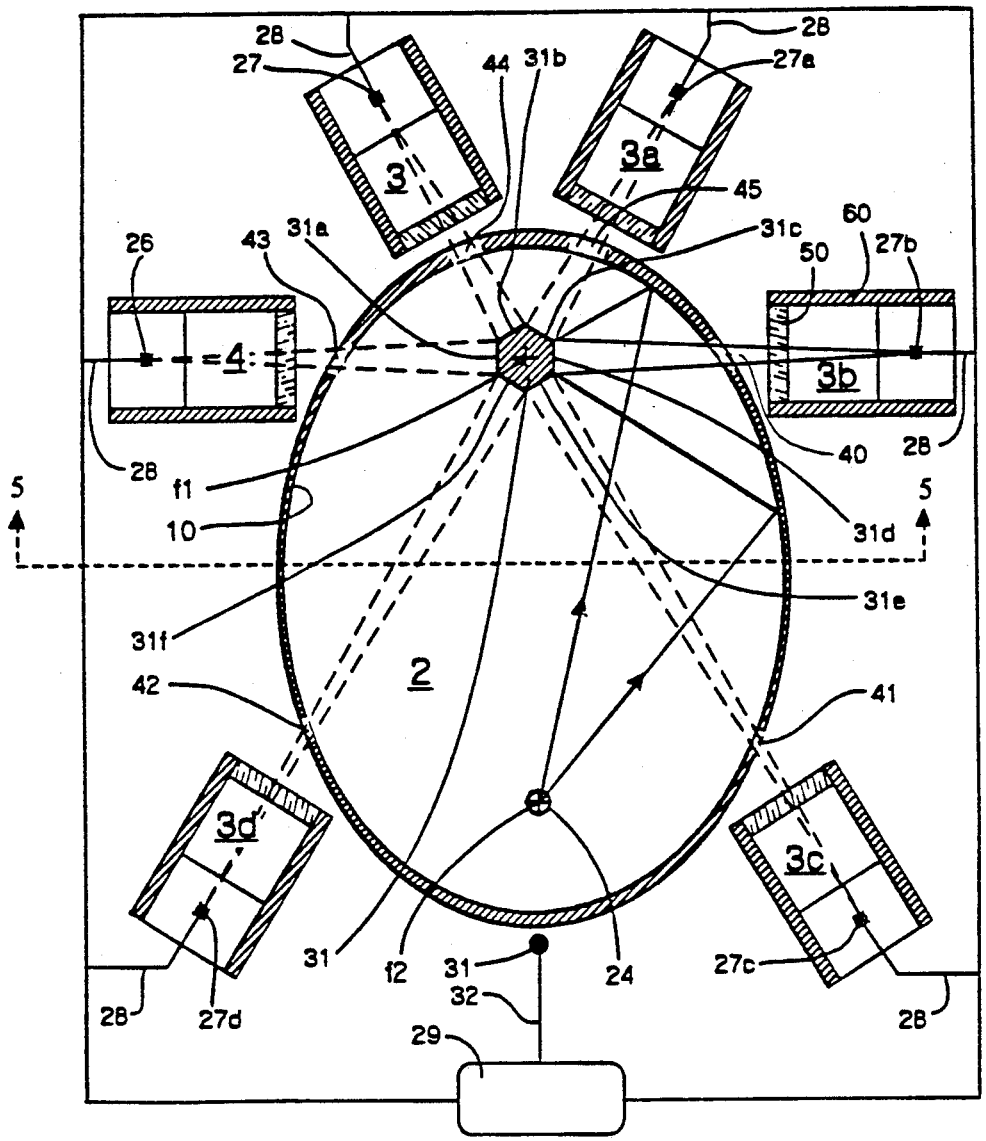
FIG. 4 is a cross-sectional plan view, taken on the line 4—4 of FIG. 5, of another embodiment of the novel analyzer.
Figure 5:
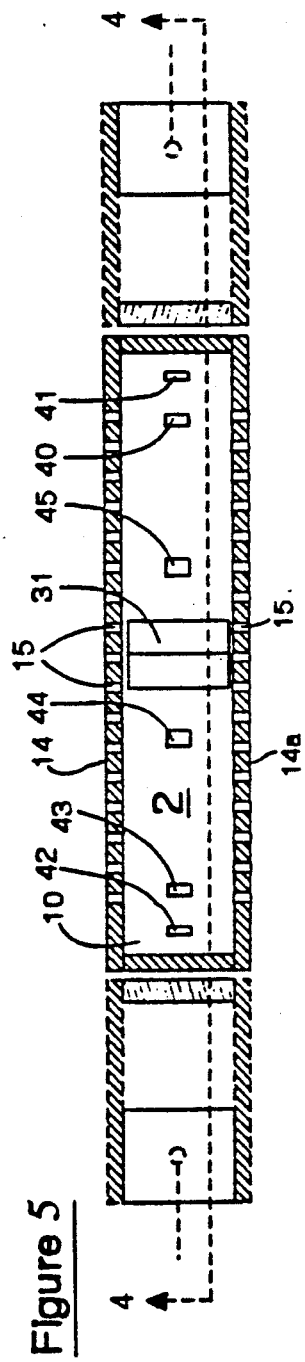
FIG. 5 is a cross-sectional side view, taken on the line 5—5 of FIG. 4, of the embodiment of FIG. 4.

FIGS. 4 and 5 illustrate a further embodiment of an analyzer for analyzing the content of several gases in an unknown sample. Like reference nunerals have been used to designated like parts.

An analyzer housing (not shown) is provided. Within the housing is a chamber 2 (hereinafter called the sample chamber) to contain the sample to be analyzed, chambers 3, 3a, 3b, 3c, and 3d (hereinafter called the analyte chambers) each containing one of the plurality of gases to be analyzed for, and a chamber 4 (hereinafter called the inert gas chamber) to contain an inert gas, which may suitably be the sample gas in which none of the analyte gases are present. The chamber 2 comprises a side wall 10, top wall 14 and bottom wall 14a. The side wall 10 is an ellipse, with its foci at f1 and f2, although it may be made as a portion of an ellipse, with a non-elliptical or several non-elliptical portions if desired. This reduces the effectiveness of the device, but may be usable if some additional power loss can be tolerated. Suitably, the side wall 10 is a material which efficiently reflects radiation, for example polished aluminum, or a composite material coated with a reflective material.

The top portion of the side wall 10 mates with a top wall 14. The bottom portion mates with a bottom wall 14a. The two walls are made of a suitable reflective material, such as polished aluminum.

Each of walls 14 and 14a is provided with a plurality of holes 15, to permit the sample gas to enter and leave the device.

At the focus f1 of the ellipse, within chamber 2, is situated a radiation source 24. The source is preferably linear and small in cross section, as can be a conventional gas chromatograph thermal conductivity detector element. One suitable such element is a Gow-Mac #13-470P element.

A multi-faceted reflective column 31 is centered at focus f2. Column 31 is approximately hexagonal in cross-section. It is preferred to deviate from a true hexagon in that a slight curvature of the reflective faces 31a, 31b, 31c, 31d, 31e, 31f, is needed to focus the radiation reflected from these faces toward the corresponding detectors 26, 27, 27a, 27b, 27c, and 27d. The column is of a suitable material and is polished, so that the faces corresponding to the sides of the hexagon reflect radiation. For example, the column can be polished aluminum.

When the source 24 is energized, radiation is focused toward the center of column 31. Each of the faces of column 31 reflects a beam of radiation toward a specific location on wall 10. For example, two rays of radiation are shown emanating from the source 24. These rays are focused toward f2 by the elliptical reflector 10. They are then reflected by face 31d toward hole 40 which penetrates wall 10. Behind hole 40 are oriented one behind the other window 50 and detector 27b, which define between them, in combination with a cylindrical side wall 60, a chamber 3b.

Similarly, other holes 41, 42, 43, 44, and 45 are shown, which receive reflections from faces 31e, 31f, 31a, 31b, and 31c respectively. In such a structure, a miltiplicity of detectors and their corresponding chambers can be provided.

With a device having six chambers, it is possible to simultaneously measure the concentrations of five analytes in the sample in chamber 2. The sixth chamber contains an inert gas, for example, the sample gas which does not contain the analyte gases.

The detectors are again connected by suitable wiring 28 to a suitable instrument control and data collection apparatus 29. For example, the apparatus 29 can include a microprocessor connected and programmed to control the timing and switching functions necessary for operating the instrument, to store and analyze the data, and to display the processed data as required.

A suitable power supply (not shwon) is provided for the source 24 and the instrument control and data collection apparatus 29. A suitable power supply is, for example, several AA size alkaline cells connected in series and/or parallel to supply the different voltages required.

If it is desired to correct for changes in ambient temperature, a thermistor 31 can be installed, and its response used in the known way to compensate the data collection apparatus 29 by wiring 32.

A suitable means for confirming proper operation of the instrument can be provided if desired. This can be done, for example, by removing a known and reproducible part of the radiation from one beam by introducing a screen into one beam, as is known in the art.

Prior to operation, the analyte chambers 3, 3a, 3b, 3c, and 3d are filled with the analyte gases and gas chamber 4 is filled with inert gas. For example, air with the carbon dioxide removed can be used in chamber 4 where the analyte is carbon dioxide, and it is intended to measure the concentration of carbon dioxide in ambient air.

The gas mixture to be analyzed is allowed to diffuse, or is otherwise introduced, into chamber 2 through holes 15. The source is energized. Since sidewall 10 is elliptical in shape, with the source 24 located at one focus f1, the radiation emitted from source 24 is focused at f2. Such radiation is then reflected by reflectors 31a, 31b, 31c, 31d, 31e, and 31f through analyte chambers 3, 3a, 3b, 3c, 3d, and inert gas chamber 4.

This focusing by the elliptical reflector onto reflecting surfaces of column 31 permits detector readings to be obtained with little expenditure of energy, allowing a relatively low-powered source to be used. It has been found, for example, that the source, the detectors and the data collection and analysis device can be operated in one embodiment on a total power of approximately 400 mw.

The data received from detectors 26, 27, 27a, 27b, 27c, and 27d are analyzed in known fashion. If the unknown sample in sample chamber 2 does not contain the analyte gas, the difference between the output of detector 26 and the other detectors will remain at a fixed known value (when corrected for temperature variation by means of thermistor 31). If, however, there is some amount of one of the analyte gases in the sample in sample chamber 2, the difference between the output of detector 26 and the detector associated with that analyte gas will exhibit a reduced value characteristic of the concentration of the analyte in sample chamber 2.

Figure 6:
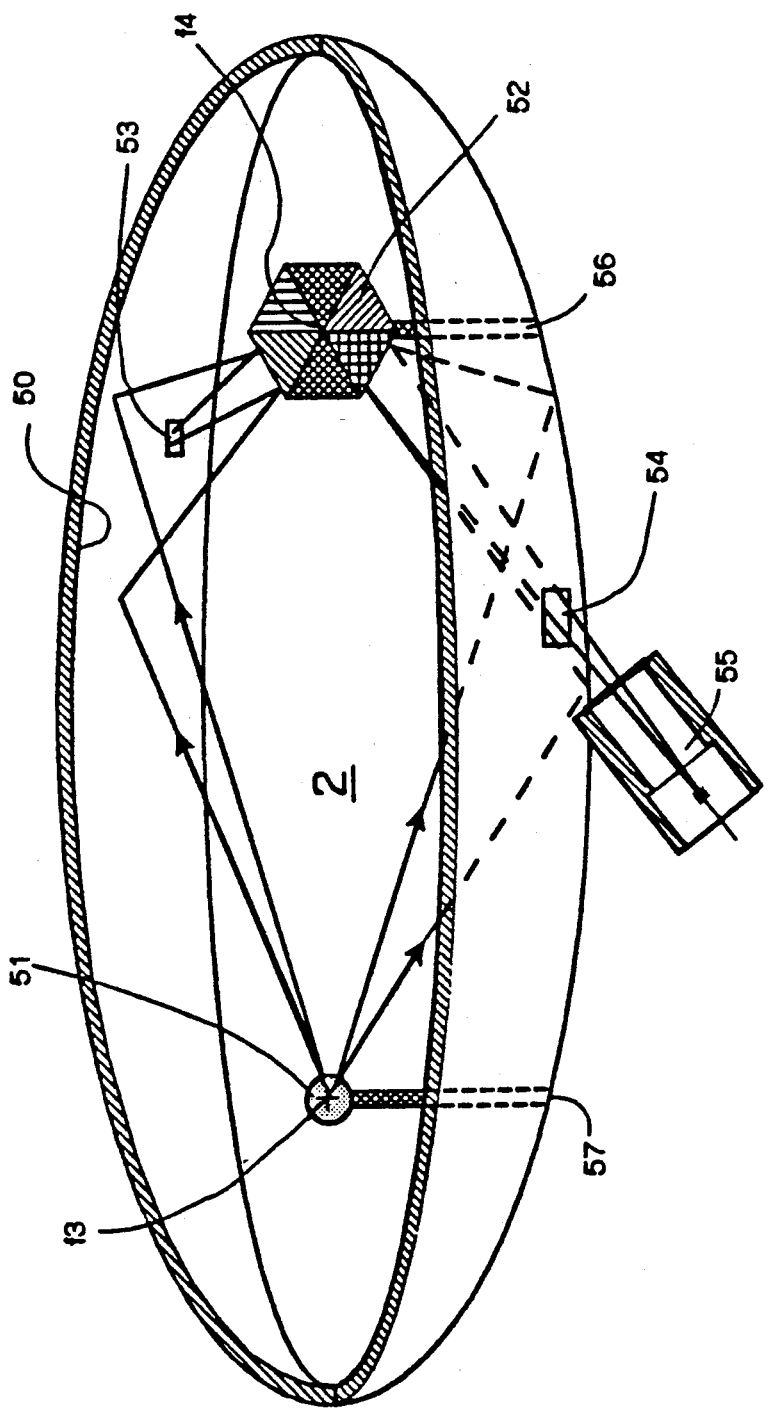
FIG. 6 is a cut-away perspective view of a further embodiment in which an ellipsoidal reflector is used to further increase the number of gases which can be measured simultaneously.

In FIG. 6 the reflector is an ellipsoid (rather than an elliptical cylinder) with f3 and f4 being the foci of the ellipsoid. Thus, the entire wall 50 is formed as an ellipsoid. A source 51, which is as close as possible being a point source, is placed at focus f3. A multifaceted reflector 52 is placed at focus f4, and holes are made in the ellipsoid at the points on the wall 50 to which the facets of reflector 52 direct the beams of radiation. Behind each of these holes is placed an analyte or inert gas chamber and a detector. Two holes 53 and 54 are shown, and one associated chamber/detector assembly 55 is shown schematically.

In the example given, only two of many possible radiation paths are shown, and the sample gas could flow, for example, through porous supports 56 and 57.

The invention has been shown with reference to certain embodiments, but it will be obvious that variations can be made by one skiled in the art without departing from the spirit of the invention, which is as set out in the appended claims.

The embodiments of the invention in which an exclusive property of privilege is claimed are defined as follows:

1. An analyzer, comprising:
   a body having a cavity having an elliptical reflecting surface means, defining a first focus and a second focus, for transmitting radiation between said focuses, a chamber for holding a sample gas to be analyzed, one of said focuses being located within said sample chamber, a chamber for holding an inert gas and a chamber for holding an analyte gas, said inert gas and analyte gas chambers being positioned along a path extending between said second focus and at least a portion of said reflecting surface means;
   a radiation source disposed at one of said focuses; and
   detector means associated with each said inert gas chamber and said analyte chamber for detecting radiation passing through said sample gas and its associated gas chamber.

2. An analyzer as defined in claim 1, said radiation means being disposed within said sample chamber, said detector means having an active element disposed at said second focus.

3. An analyzer as defined in claim 2, said sample gas chamber, said inert gas chamber and said analyte chamber being in gas tight relation to one another.

4. An analyzer as defined in claim 1, further including divider wall means for sealingly separating said inert gas chamber and said analyte chamber from one another and preventing the exchange of radiation therebetween.

5. An analyzer as defined in claim 1, further including transparent window means for sealingly separating said sample chamber from each said inert gas chamber and said analyte chamber while permitting the transmission of radiation therebetween.

6. An analyzer as defined in claim 5, further including means for admitting a sample gas into said sample chamber.

7. An analyzer as defined in claim 6, said admitting means including apertures in said body for permitting ambient air to diffuse into said sample chamber.

8. An analyzer as defined in claim 1, further including a plurality of said analyte chambers.

9. An analyzer as defined in claim 1, said body having a side wall and opposed end walls defining said cavity, at least a portion of said side wall having an elliptical cylindrical inner surface defining said reflecting surface whereby each said focus being a focal axis paralleling said side wall, a transparent window extending across said side wall between said focal axes so as to define said sample chamber with said opposed end walls and said side wall, and at least one divider wall extending between said side wall and said window remote from said sample chamber and defining therewith said inert gas chamber and said analyte chamber.

10. An analyzer as defined in claim 9, said radiation source being disposed along said focal axis within said sample chamber and said detector means comprising a gas detector disposed at the focal axis extending through each said inert gas chamber and said analyte chamber.

11. A nondispersive gas analyzer for use in monitoring the concentration one or more gases, comprising:
   a body having a side wall and opposed end walls defining a cavity, at least a portion of said side wall having a reflective elliptical cylindrical inner surface defining a first focal axis and a second focal axis paralleling said side wall, a transparent window extending across said cavity transversely of a plane containing said focal axes and being in gas tight engagement between said side wall and said opposed end walls so as to define therewith a sample chamber for a sample gas to be analyzed, at least one divider wall extending perpendicularly of said focal axes and said window on a side thereof remote from said sample chamber, said divider wall being in gas sealing engagement with said body and said window so as to define an inert gas chamber and an analyte chamber, said first focal axis extending through said sample chamber and said second focal axis extending through each said inert gas chamber and said analyte chamber, said body having means for admitting ambient gases into said sample chamber;
   a radiation source disposed within said sample chamber along said first focal axis; and
   a detector associated with said inert gas chamber and each said analyte chamber for producing an electrical signal representative of the radiation passing through said sample gas and the analyte gas contained within its associated chamber.

12. A gas analyzer, comprising:
   a body having a chamber for holding a sample gas to be analyzed, said sample gas chamber having a reflective inner surface, at least a portion of said inner surface being elliptical and defining a first focus and a second focus within said sample gas chamber and being operable to reflect radiation between said focuses;
   a sealed inert gas chamber for holding an inert gas;
   a sealed analyte gas chamber for holding an analyte gas;
   a radiation source disposed at said first focus in said sample gas chamber;
   means disposed around said second focus for reflecting radiation emitted by said radiation source and focused by said reflective inner surface toward each said sealed gas chambers; and detector means associated with each said sealed gas chambers for detecting radiation which was emitted by said source and which has travelled through said sample gas and the gas in its associated sealed gas chamber and for producing a signal representative of the concentration in said sample gas of the gas contained in its associated sealed gas chamber.

13. A gas analyzer as defined in claim 12, said portion of said reflective inner surface being in the form of an elliptic cylinder, said first focus and said second focus being first and second axes, respectively.

14. A gas analyzer as defined in claim 13, said reflector means being a multisided column coaxially disposed along said second focal axis and defining a plurality of reflective surfaces paralleling said second focal axis and each being operable to reflect radiation emitted by said source and focused by said reflective inner surface toward a predetermined one of said inert gas and analyte chambers.

15. A gas analyzer as defined in claim 14, said column being hexagonal.

16. A gas analyzer as defined in claim 13, further including a plurality of said analyte gas chambers for holding one of a plurality of different analyte gases.

17. A gas analyzer as defined in claim 13, said radiation means being disposed within said sample gas chamber.

18. A gas analyzer as defined in claim 13, further including means for admitting a sample gas into said sample gas chamber.

19. A gas analyzer as defined in claim 18, said admitting means including apertures in said body for permitting ambient gas to diffuse into said sample gas chamber.

20. A nondispersive, infrared gas analyzer, comprising:
- a body having a chamber for holding a sample gas to be analyzed, said sample gas chamber having a top wall, a bottom wall and a reflective side wall in the form of an elliptical cylinder extending between said top and bottom walls and defining a first focal axis and a second focal axis, and means for admitting a sample gas into said sample gas chamber;
- a linear infrared radiation source of small cross section disposed along said first focal axis in said sample gas chamber;
- a column coaxially disposed along said second focal axis, said column having a plurality of reflective surfaces, each of said plurality of reflective surfaces being operable to reflect radiation emitted by said radiation source and reflected by said side wall to a predetermined location on said side wall;
- a plurality of sealed gas chambers disposed outside of said sample gas chamber for containing one of a plurality of gases, one of said sealed gas chambers being operable to contain an inert gas, each said sealed gas chamber having a partition transparent to radiation emitted by said radiation source and disposed at one of said locations on said side wall; and
- a detector associated with each said sealed gas chambers for detecting radiation source originating radiation which has travelled through said sample gas and the gas in its associated sealed gas chamber and for producing a signal representative of the concentration in said sample gas of the gas contained in its associated sealed gas chamber.

21. A gas analyzer as defined in claim 12, said portion of said inner surface being in the form of an ellipsoid.

22. A gas analyzer as defined in claim 21, said reflector means being a polygon centered at said second focus and having a plurality of reflective surfaces, each reflective surface of said plurality of reflective surfaces being operable to reflect radiation emitted by said source toward a predetermined one of said sealed gas chambers.

23. A gas analyzer as defined in claim 21, further including a plurality of said analyte gas chambers for holding one of a plurality of different analyte gases.

24. A gas analyzer as defined in claim 21, said radiation source being disposed within said sample gas chamber.

25. A gas analyzer as defined in claim 21, further including means for admitting a sample gas into said sample gas chamber.

26. A gas analyzer as defined in claim 25, said admitting means including apertures in said body for permitting ambient gas to diffuse into said sample gas chamber.

27. A nondispersive, infrared gas analyzer, comprising:
- a body having a chamber for holding a sample gas to be analyzed, said sample gas chamber having a top wall, a bottom wall and a reflective side wall in the form of an ellipsoid, said side wall defining a first focus and a second focus, and said body having means for admitting a sample gas into said sample gas chamber;
- a infrared radiation source of small cross section disposed at said first focus in said sample gas chamber;
- a polygonal body centered on said second focus and having a plurality of reflective surfaces, each surface of said plurality of reflective surfaces being operable to reflect radiation emitted by said radiation source and focused by said inner wall to a predetermined location on said inner wall;
- a plurality of sealed gas chambers disposed on the outside of said sample gas chamber containing one of a plurality of gases, one of said sealed gas chambers being operable to contain an inert gas, each said sealed gas chamber having a partition transparent to radiation emitted by said radiation source and disposed at one of said locations on said inner wall; and
- a detector associated with each said sealed gas chambers for detecting radiation originating at said radiation source which has travelled through said sample gas and the gas in its associated sealed gas chamber and for producing a signal representative of the concentration in said sample gas of the gas contained in its associated sealed gas chamber.

* * * * *